(12) United States Patent
Wohlschlager et al.

(10) Patent No.: US 11,175,781 B2
(45) Date of Patent: Nov. 16, 2021

(54) OPERATION CONTROL OF WIRELESS SENSORS

(71) Applicant: KONINKLIJKE PHILIPS N.V., Eindhoven (NL)

(72) Inventors: Markus Wohlschlager, Sindelfingen (DE); Albrecht Reinhard Kinzkofer, Bondorf (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 522 days.

(21) Appl. No.: 16/300,075

(22) PCT Filed: May 31, 2017

(86) PCT No.: PCT/EP2017/063100
§ 371 (c)(1),
(2) Date: Nov. 9, 2018

(87) PCT Pub. No.: WO2017/211636
PCT Pub. Date: Dec. 14, 2017

(65) Prior Publication Data
US 2020/0305839 A1  Oct. 1, 2020

(30) Foreign Application Priority Data

Jun. 7, 2016  (EP) .................................... 16173274

(51) Int. Cl.
*A61B 8/08* (2006.01)
*G06F 3/044* (2006.01)
(Continued)

(52) U.S. Cl.
CPC ............ *G06F 3/044* (2013.01); *A61B 8/4209* (2013.01); *A61B 8/465* (2013.01); *A61B 8/467* (2013.01);
(Continued)

(58) Field of Classification Search
CPC combination set(s) only.
See application file for complete search history.

(56) References Cited

U.S. PATENT DOCUMENTS 8,290,596 B2    10/2012  Wei
2003/0139664 A1*  7/2003  Hunt ................... G01S 7/52023
                                                               600/407
(Continued)

FOREIGN PATENT DOCUMENTS

DE    102013216152    2/2015
JP        05245140 A    9/1993
(Continued)

*Primary Examiner* — Hien L Duong

(57) ABSTRACT

The invention relates to a method for controlling an ultrasound system comprising at least two ultrasound sensor units using gestures. The method comprises: detecting a gesture on a first ultrasound sensor unit; matching the detected gesture to one of the plurality of gestures in the gestures database; reading the assigned at least one system function in the gesture database related to the detected gesture; and activating the at least one system function. At least one system function includes switching a sound source from a second ultrasound sensor unit to said first ultrasound sensor unit and wherein the gesture assigned to this system function comprises a double-tap on the surface of the first ultrasound sensor unit. Further, the invention relates to a system for carrying out the method.

15 Claims, 6 Drawing Sheets

(51) Int. Cl.
*A61B 8/00* (2006.01)
*G06F 3/01* (2006.01)
*G06F 3/0481* (2013.01)
*G06F 3/0488* (2013.01)
*G16H 40/63* (2018.01)

(52) U.S. Cl.
CPC ............... *A61B 8/54* (2013.01); *G06F 3/017* (2013.01); *G06F 3/0481* (2013.01); *G06F 3/04883* (2013.01); *G16H 40/63* (2018.01); *A61B 8/4472* (2013.01)

(56) References Cited

U.S. PATENT DOCUMENTS

| | | | | |
|---|---|---|---|---|
| 2004/0152982 A1* | 8/2004 | Hwang | ............... | A61B 8/4433 600/441 |
| 2006/0058654 A1* | 3/2006 | Di Marco | ............ | A61B 8/4477 600/437 |
| 2007/0066894 A1* | 3/2007 | Bartol | ............... | A61B 8/00 600/437 |
| 2010/0063398 A1* | 3/2010 | Halmann | ............ | A61B 8/4236 600/459 |
| 2010/0168578 A1* | 7/2010 | Garson, Jr. | ............ | A61B 8/0858 600/443 |
| 2010/0191120 A1* | 7/2010 | Kraus | ............... | A61B 8/481 600/459 |
| 2012/0232391 A1* | 9/2012 | Kojima | ............... | A61B 8/4477 600/443 |
| 2013/0178744 A1* | 7/2013 | Kierulf | ............... | A61B 8/467 600/459 |
| 2013/0245436 A1* | 9/2013 | Tupin, Jr. | ............... | A61B 5/344 600/430 |
| 2014/0024940 A1 | 1/2014 | Yoneyama | | |
| 2014/0114190 A1* | 4/2014 | Chiang | ............... | A61B 8/4405 600/440 |
| 2014/0121524 A1* | 5/2014 | Chiang | ............... | G01S 7/52023 600/459 |
| 2014/0128739 A1 | 5/2014 | Sundaran | | |
| 2014/0200449 A1* | 7/2014 | Yoo | ............... | A61B 8/461 600/437 |
| 2015/0065881 A1* | 3/2015 | Cho | ............... | A61B 8/4472 600/443 |
| 2016/0062489 A1* | 3/2016 | Li | ............... | G06F 3/0346 345/163 |
| 2016/0106396 A1* | 4/2016 | Jin | ............... | A61B 8/4477 600/437 |
| 2016/0120508 A1* | 5/2016 | Kim | ............... | A61B 8/54 600/443 |
| 2016/0259515 A1* | 9/2016 | Sabina | ............... | G06F 3/04883 |
| 2016/0317131 A1* | 11/2016 | Klessel | ............... | A61B 8/54 |
| 2017/0074837 A1* | 3/2017 | Lee | ............... | G01S 15/8963 |
| 2018/0103926 A1* | 4/2018 | Morikawa | ............ | A61B 8/5269 |
| 2019/0059856 A1* | 2/2019 | Jin | ............... | A61B 8/4472 |
| 2020/0064995 A1* | 2/2020 | Corsica | ............... | G06F 3/0484 |

FOREIGN PATENT DOCUMENTS

| | | |
|---|---|---|
| JP | 11105646 A | 4/1999 |
| JP | 2011136164 A | 7/2011 |
| JP | 2015202247 A | 11/2015 |
| WO | 2015/005796 | 1/2015 |

\* cited by examiner

| Gesture ID | Gesture Label | Reference Sensor Data | System Function | ... |
|---|---|---|---|---|
| 001 | Tap | 280, 110, 332... | Mouse click | |
| 002 | Double Tap | 420, 200, 504... | Initiate GUI control mode | |
| 003 | Pattern 1 | 543, 123, 535... | Settings configuration 1 | |
| 004 | Triple Tap | 645, 745, 856... | Personnel alert | |
| ... | | | | |

FIG. 3

OPERATION CONTROL OF WIRELESS SENSORS

CROSS REFERENCE TO RELATED APPLICATIONS

This application is the U.S. National Phase application under 35 U.S.C. § 371 of International Application No. PCT/EP2017/063100, filed May 31, 2017 published as WO 2017/211636 on Dec. 14, 2017, which claims the benefit of European Patent Application Number 16173274.8 filed Jun. 7, 2016. These applications are hereby incorporated by reference herein.

BACKGROUND OF THE INVENTION

Wireless registration of medical parameters is a contemporary trend. The progress in battery technology as well as the miniaturization of radio and signal processing allows the acquisition of many physiological signals with wireless means, where cables used to have been necessary. One major advantage of wireless technology is to spatially separate the base device from the sensors and to give the patient more freedom of movement. With cable bound solutions, the range of use is limited to the length of the cable. For many sensors, the cable length is typically between 2-2.5 m, this is roughly the distance which can be covered with outstretched arms. Some parameters require initial or permanent adjustments during placement or operation.

For example, an electronic fetal monitor typically has two sensors, an ultrasound Doppler sensor for monitoring the fetal heart rate and a TOCO sensor for registering the uterine contractions. Both sensors require control actions during placement and operation. For these control actions, the base devices provide push buttons, rotary knobs or a touchscreen. With cables, the distance between sensor and the operation controls is limited in a way that sensor positioning and operational adjustments can be done with two hands. One hand is, for instance, searching the optimum placement position of the ultrasound sensor and the other is controlling the sound volume of the acoustical heart beat output. Luckily, the distance between the base device and the wireless sensors is not limited to a short distance.

The need to keep the wireless sensors in a reachable proximity of the base device during placement or readjustment is an unacceptable and unnecessary limitation. For workflow simplification, it would be helpful to have essential operating controls on spot. For a fetal ultrasound Doppler sensor, the essential operating controls are, for example, the sound source selection and the volume control of the acoustical output. Integration of operating control buttons into the housing of a sensor is normally no problem, but under certain boundary conditions, typical mechanical control elements like push buttons, switches or rotary knobs are difficult to realize. Important design conditions preventing an implementation with traditional operation control elements are water tightness, disinfectant-proofness, sterilization and disinfection, housing size/restrictions, operation with gloves, miniaturization, cost, etc. Additional and/or alternative drawbacks of these and/or other approaches may be presented.

For all the reasons listed before, a simple, cost-efficient solution, based on a new method and system of control is necessary.

German Pat. App. No. DE102013216152 discloses an ultrasound device for medical diagnosis and therapy, which comprises a wireless ultrasonic head with a control means that is able to detect gestures via an optical camera and an accelerometer. The disclosed ultrasound device is controlled by making gestures such as tapping and swiping.

US 2013/0178744 A1 discloses an ultrasound system that includes an ultrasound probe comprising an ultrasound transducer and a touchzone configured to detect a sliding gesture of one or more digits. By means of the touchzone, manual inputs or commands can be received from a caretaker's hand without the caretakers fingers having to be displaced or separated from the probe. In addition, the touchzone facilitates an entry of commands utilizing non-sliding gestures such as tapping against the touch zone.

US 2014/0128739 A1 discloses an ultrasound imaging system with an ultrasound probe comprising a motion sensing system for detecting gestures or specific patterns of movement performed with the probe. Based on the detected gesture, a control operation is performed. In addition, the ultrasound probe may comprise a trackpad for controlling the position of a cursor on a display device. Further, the probe may include a pair of buttons to interact with a graphical user interface, or the user may interact with the graphical user interface through the trackpad and perform actions such as tap or double-tap on the track pad to access the functionality of the buttons.

SUMMARY OF THE INVENTION

In accordance with a first aspect, the invention suggests a method for controlling an ultrasound system comprising at least two ultrasound sensor units using gestures, each ultrasound sensor unit comprising a sensor for gesture detection on the surface of the ultrasound sensor unit. The method comprises: detecting a gesture on a first ultrasound sensor unit; determining if the detected gesture matches one of a plurality of gestures stored in a gestures database; matching the detected gesture to one of the plurality of gestures in the gestures database; reading the assigned at least one system function in the gesture database related to the detected gesture; and activating the at least one system function. At least one system function includes switching a sound source from a second ultrasound sensor unit to said first ultrasound sensor unit and the gesture assigned to this system function comprises a double-tap on the surface of the first ultrasound sensor unit.

In a further aspect, the invention suggests an ultrasound system comprising at least two ultrasound sensor units controllable using gestures, each ultrasound sensor unit comprising a sensor for gesture detection on the surface of the ultrasound sensor unit. The system is configured to determine if a gesture detected on a first ultrasound sensor unit matches one of a plurality of gestures stored in a gestures database, to match the detected gesture to one of the plurality of gestures in the gestures database, to read the assigned at least one system function in the gesture database related to the detected gesture, and to activate the at least one system function. At least one system function includes switching a sound source from a second ultrasound sensor to said first ultrasound sensor and wherein gesture assigned to this system function comprises a double-tap on the surface of the first ultrasound sensor unit.

The gesture database may store a plurality of gestures. In this case, it is determined if the detected gesture matches one of the plurality of gestures stored in the gesture database and the detected gesture is matched to the gesture in the gesture database to read the assigned at least one system function in the gesture database related to the detected gesture.

In one embodiment of the invention, the method further comprises detecting a gesture via an at least one sensor and storing the detected gesture as a gesture template in a gesture template database. The stored gesture template is then assigned an at least one system function. The method further comprises performing a gesture detectable via the at least one sensor and determining a stored gesture template that matches the performed gesture. The assigned at least one system function is then determined based on the determined matching stored gesture template and is activated in the wireless health monitoring system. The system comprises a base unit, an at least one sensor, and a graphical user interface (GUI) on a display.

In various embodiments, the method described herein may include an ultrasound device that detects a gesture via at least one sensor, the at least one gesture representing at least one system function and often a plurality of system functions. The detected gesture may be compared to stored gestures in a gesture template database and the at least one system function and/or plurality of system functions may be similarly stored in the gesture template database and associated with a particular gesture template. Once stored, the gesture may be performed on the ultrasound device and may also be detectable thereon by the at least one sensor on the device. The system and method may determine if any of the plurality of the stored gestures in the gesture database match the performed and detected gesture and if so determine the assigned at least one system function based associated with the stored gesture. If a match is detected and determined, the at least one system function may be activated.

In various embodiments, the system may include an ultrasound device and sensor unit that may be manipulated by a user. The ultrasound device may include a sensor module, an audio output device, an accelerometer, a communication module and a power source. The device may include the sensor for detecting gesture input and the communication module may allow communication between the device and a base unit. The audio output device of the sensor module may, in some variations, include an audio output in the base unit, either of which could utilized standard signal processing and which generates a data stream of audio data, the audio data emitted from the audio output device on either of the sensor module or the base unit. The base unit may include a communication module, power source and processor along with either an integrated or non-integrated gesture database stored in a memory. In some aspects, the gesture database may also be populated from the base unit to an associated device which, when docked for charging, receives the gesture database and can maintain a copy of the database locally. The processor may as well include associated memory for storing instructions to implement the various aspects and methods of the system described herein. Further, a graphical user interface may be integrated with the base unit or separate therefrom with an associated display.

The system of the invention includes a first and a second ultrasound device for sound source switching between two sensors for the fetal monitoring of twins. Alternatively, the system and method disclosed herein may support any of a plurality of ultrasound transducers, such as for example when detecting the fetal heart rate of triplets. In some instances of such implementations, two ultrasound devices and sensors may be utilized and may be integrated by electronic communication with the base unit. Typically, as only one of the two sensors may be used as the source of the acoustical output to monitor and both sensors may be attached to a patient's abdomen for monitoring both or multiple fetal hearts. In such a multi-heart rate application and mode implementation, the operator may switch between the sound-sources by a control gesture on the sensor/ultrasound device. The inactive device (any device which is currently not providing any sound data) may sense the gesture input, switch sound-source inputs forwarded to the base unit and allow the other heard to be monitored. After detecting the performed gesture by the sensor, the sound-source-switch is activated and the inactive sensor becomes the source ultrasound device. The base unit may be in electronic communication with the sensors/ultrasound devices to conveniently allow the source to be switched as needed.

In implementations, the present disclosure sets forth a method for controlling an ultrasound device using gestures, comprising: detecting a gesture from an ultrasound sensor unit; providing the detected gesture to a base unit by electronic communication; determining if the detected gesture matches one of a plurality of gestures stored in a gestures database; matching the detected gesture to one of the plurality of gestures in the gestures database; reading the assigned at least one system function in the gesture database related to the detected gesture; activating the at least one system function in the sensor unit.

These and other implementations may each optionally include one or more of the following features. For instance, the features may include wherein wherein the detecting of the gesture is through a capacitive sensors. The features may include populating the gesture database by storing the detected gesture as a gesture template in the gesture database; assigning an at least one system function to the stored gesture in the gesture database; including with the detected gesture a plurality of reference sensor data. The features may include activating mouse-type input mode at the ultrasound sensor unit by recognizing an associated mouse-type input mode gesture; interpreting control gestures on the ultrasound sensor unit for an associated graphical user interface display. As well, the features may include interpreting control gestures relates to input on the graphical user interface display.

Further, a system for controlling an ultrasound device using gestures may comprise: an ultrasound sensor unit including an ultrasound sensor module, a plurality of capacitive sensors and a communication module; a base unit including a processor and memory and a base unit communication module; a control gesture data database accessible by the processor of the base unit; wherein the memory on the base unit includes instructions which, when executed by the processor, operate to: detect gesture sensor data from at least one of the capacitive sensors, the gesture sensor data representing a gesture; provide the detected gesture sensor data to a base unit by electronic communication; determine if the detected gesture sensor data matches one of a plurality of gestures stored in the gestures database; read the assigned at least one system function in the gesture database related to the determined matched gesture; activate the at least one system function in the sensor unit.

Other implementations may each optionally include one or more of the following features. The memory on the base unit further includes instructions which, when executed by the processor, operate to: switch a sound source from the first ultrasound sensor unit to the second ultrasound sensor unit. The features may include when determining if the detected gesture sensor data matches one of a plurality of gestures stored in the gestures database includes comparison of gesture sensor data with a plurality of stored gesture sensor data in the gesture database. The features may include wherein the memory on the base unit further includes instructions which, when executed by the processor, operate to: populate the gesture database by storing the detected gesture sensor data as a gesture template in the gesture database; assign an at least one system function to the stored gesture in the gesture database; include with the detected gesture sensor data a gesture identifier.

Other features may include wherein the base unit is further operable to activate mouse-type input mode at the ultrasound sensor unit by recognizing an associated mouse-type input mode gesture; interpret control gestures on the ultrasound sensor unit for an associated graphical user interface display, wherein the control gestures relate to input on a graphical user interface display.

Other aspects may include corresponding methods, systems, apparatus, and computer program products.

Other implementations may include one or more non-transitory computer readable storage media storing instructions executable by a processor (e.g., a central processing unit (CPU) or graphics processing unit (GPU)) to perform a method such as one or more of the methods described above. Yet another implementation may include a system of one or more computers that include one or more processors operable to execute stored instructions to perform a method such as one or more (e.g., all) aspects of one or more of the methods described above.

It should be appreciated that all combinations of the foregoing concepts and additional concepts described in greater detail herein are contemplated as being part of the subject matter disclosed herein. For example, all combinations of claimed subject matter appearing at the end of this disclosure are contemplated as being part of the subject matter disclosed herein.

BRIEF DESCRIPTION OF THE DRAWINGS

The accompanying drawings, which are included to provide a further understanding of the disclosure, are incorporated herein to illustrate various embodiments. In the drawings:

FIG. 3 illustrates a gesture template database according to the description presented herein.

DETAILED DESCRIPTION OF EMBODIMENTS

Figure 1:
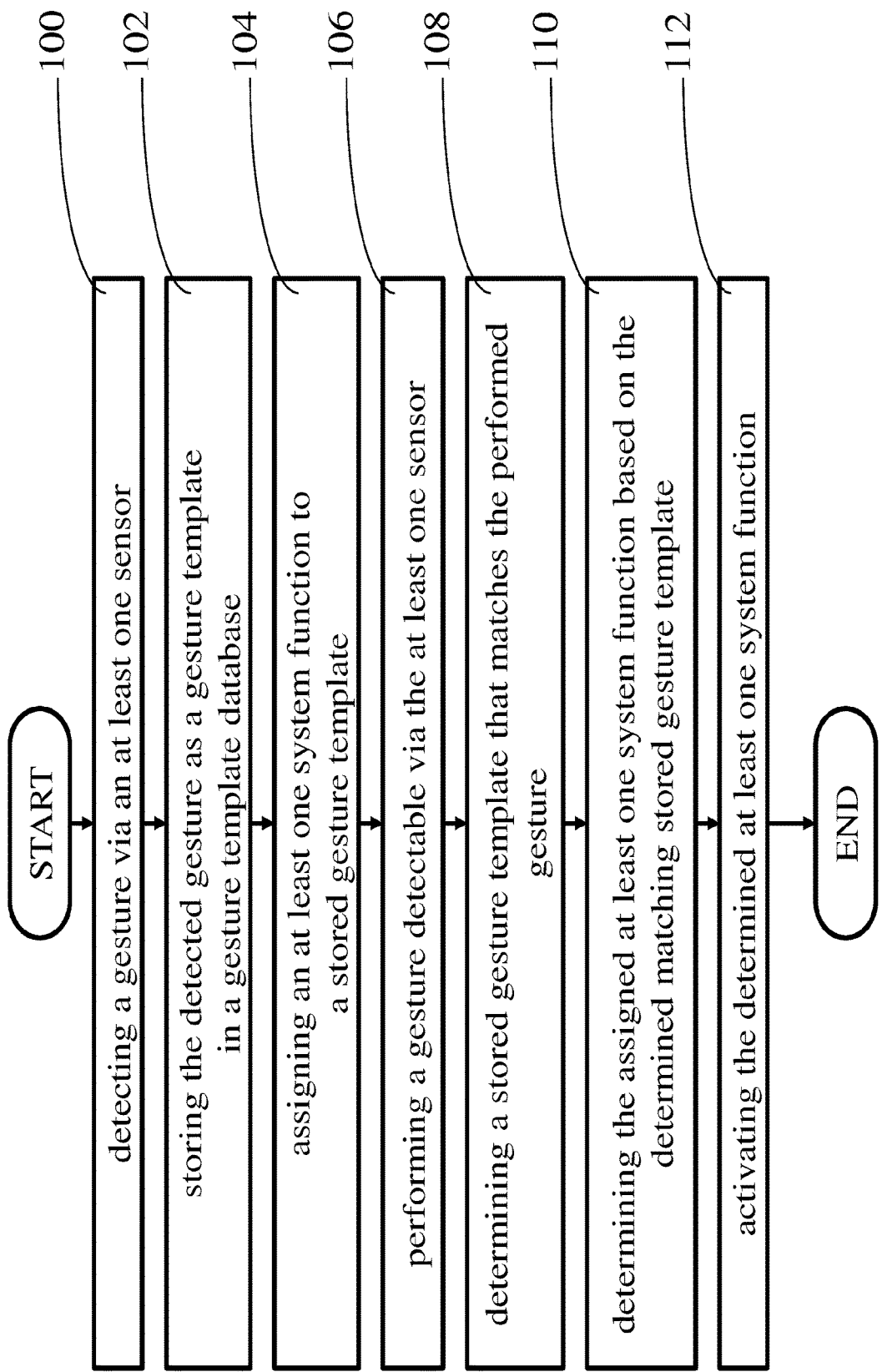
FIG. 1 is a flowchart illustrating a method for controlling a wireless health monitoring system via gestures according to one embodiment.

In some implementations of the technology described herein, an ultrasound sensor may be utilized having a sensor input to detect various gestures or input from an operator that is operating the ultrasound device. The ultrasound device may further include, in various implementations, a base unit with which it is in electronic communication and which may include a gestures database for storing both the gestures and associated functions for the ultrasound device(s).

The following are terms used in the in the description for the various embodiments set out herein.

The term "health monitoring" as used herein may in some aspects refer to the monitoring or measurement of a patient's physiological parameters such as those performed during pregnancy, labor and delivery. The systems used for health monitoring may include devices such as an ultrasound device.

The term "sensor" as used herein may in some embodiments refer to the ultrasound device component that is used to monitor the fetal and maternal physiological parameters. An example of a "sensor" as used herein may be an accelerometer or a transducer such as an ultrasound transducer.

The term "gesture" as used herein may in some aspects refer to any movement or motion by one or more body parts such as a finger that permits the control or operation of a device without having to use physical buttons or knobs, for example. The use of these gestures may be implemented using touch sensitive surfaces such as capacitive or resistive surfaces including touchscreens. Examples of gestures employable in one embodiment include a tap, a double-tap, swiping motions, or any combination thereof, among others.

The technology disclosed herein may include a method and system for controlling a wireless health monitoring system. The method may comprise: detecting a gesture via an at least one sensor; storing the detected gesture as a gesture template in a gesture template database; assigning an at least one system function to a stored gesture template; performing a gesture detectable via the at least one sensor; determining a stored gesture template that matches the performed gesture; determining the assigned at least one system function based on the determined matching stored gesture template; and activating the determined at least one system function.

The technology set forth herein may also relate to a system for controlling a wireless health monitoring system. The system may include a base unit for processing signals; a sensor unit that records signals relating to health monitoring; an at least one sensor connected to the sensor unit for detecting gestures and a graphical user interface (GUI) for interacting with the system.

Many medical sensors, especially the sensors used for health monitoring, have built-in accelerometers. The accelerometers are used for various purposes such as pulse rate detection, movement and posture detection, or fall detection. Some of the accelerometers already have a built-in tap or double-tap detection. In the simplest implementation, the tap functionality could be used to activate a specific function of one of a plurality of sensors. For example, for the fetal monitoring of twins, two sensors are placed on the mother's abdomen. Only one of the sensors can be used as the source of the acoustical Doppler sound, but if one needs to reposition the second sensor, the source of the acoustical output must be switched to the second sensor.

The present disclosure provides a solution to such prior issues by allowing sound source switching on the spot using gestures such as tap or double-tap. The functionality triggered by the tap can be sensor-type dependent, thus, allowing different actions. Besides the possibility of a focus change, the tap action could be used to enable an interpretation mode of the accelerometer data for a certain time.

In one aspect described herein, an interpretation mode is one of the possible several modes that the accelerometer or the wireless health monitoring system of the present invention can be switched to in accordance with the present invention. This mode allows the device to interpret and identify the corresponding conventional functional equivalent (such as those of a conventional hardware controlled by physical buttons and knobs) intended to be replaced by the assigned inputted gesture functionality. In this mode for example, a rotational movement in a plane could be interpreted as a rotation of a rotary knob to control the sound volume. Many other predefined gestures may be used, for example, shift movements up or down, shift movements left and right, etc. The accelerometer could also be used to provide an input mode akin to that of a virtual mouse. After switching to the interpretation mode, via a tap or double-tap, a gesture could be used to position the cursor on an operation panel of the base unit and activate the underlying functionality of the selected control button on the panel by a tap or double-tap, for example. Activation of the interpretation mode is not limited to activation by tapping. Proximity detectors or other means could also be used to enable such functionality.

FIG. 1 depicts a flowchart illustrating an exemplary method for controlling a wireless health monitoring system via gestures according to one aspect. A gesture is detected via an at least one sensor (step 100) and is then stored as a gesture template in a gesture template database 218 (step 102). The stored gesture template is assigned an at least one system function according to user preference (step 104). When the user performs a gesture detectable via the at least one sensor (step 106), the system determines the stored gesture template from the gesture template database that most closely matches the detected gesture (step 108). The assigned at least one system function for the identified gesture is determined (step 110) and the corresponding system function is then activated (step 112).

Determination of the gesture template matching the detected gesture may be done at the base unit which may have a copy of the gesture database. Alternatively, the gesture database may be stored at the sensor unit which may have both associated memory for storage of such database and instructions and a processor for executing instructions to match such template and detected gesture.

System functions that can be activated preferably include a sound source switching, a volume adjustment, and a mouse-type input. Preferably, the gesture template can activate more than one system function successively or simultaneously.

In another aspect, preferably only authorized users, such as doctors and medical technicians, are permitted to create and store customized or personalized gestures in the gesture template database, and also to assign their preferred system functions corresponding to the customized gesture templates they created. Hence, the users are not limited to simple, pre-stored gesture templates, such as tapping and directional swiping, but are allowed the flexibility to choose their own preferred gestures based on convenience or because of some physical limitations. Preferably, the system allows the creation of more complex control gestures and the assignment to those gestures of highly specialized system functions, for example, using one relatively complex gesture to perform an equivalent of two separate functions performed successively.

Figure 2:
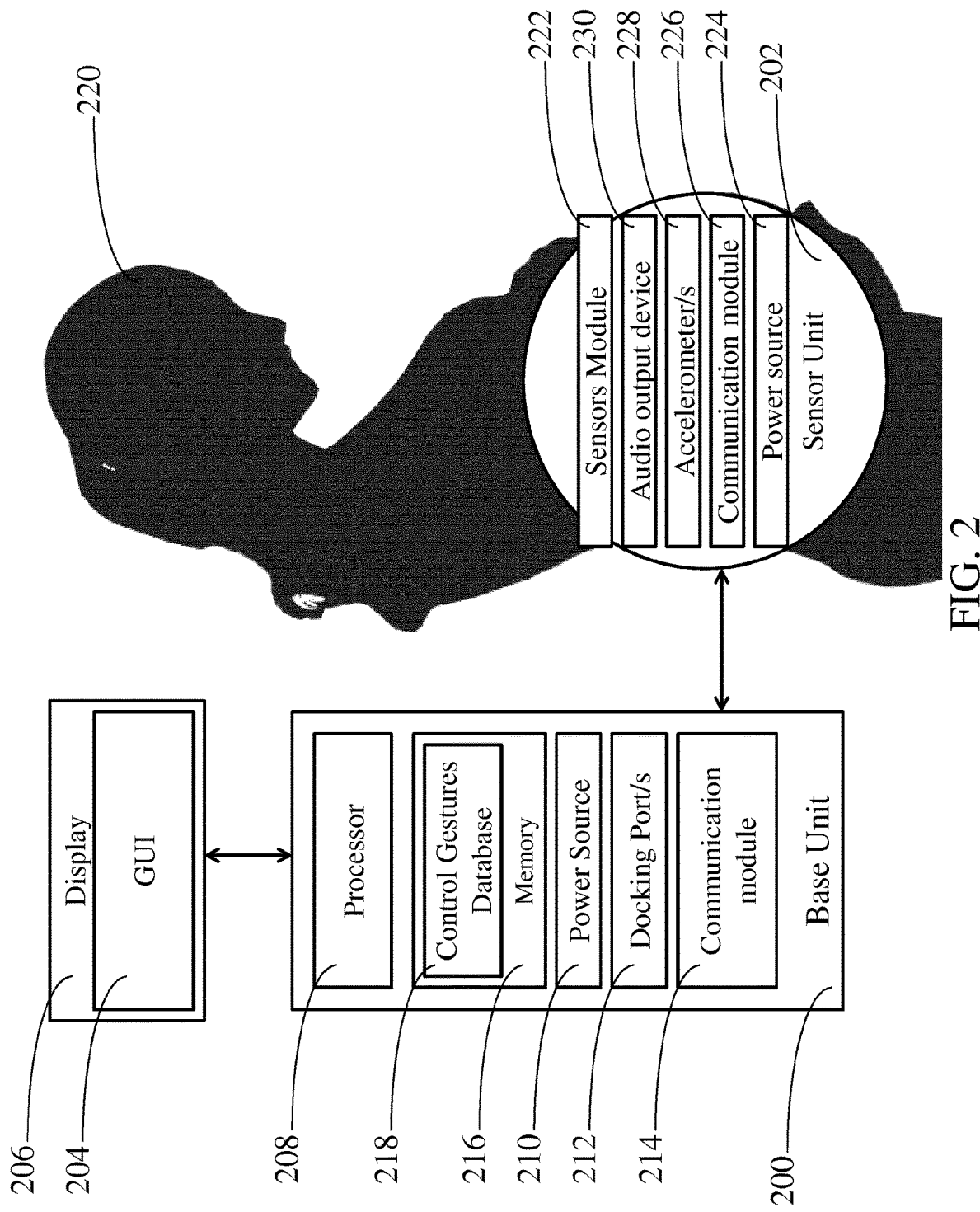
FIG. 2 is a block diagram of a wireless health monitoring system controlled by gestures according to another embodiment.

FIG. 2 illustrates another embodiment of a wireless health monitoring system. As shown in FIG. 2, the wireless health monitoring system comprises a base unit 200, a sensor unit 202 and a graphical user interface (GUI) 204 shown on a display device 206. The base unit 200 comprises a processor 208, a power source 210, an at least one docking port 212, and a communication module 214. The base unit 200 further comprises a memory 216 for storing gesture template database 218. When attached to a patient 220, the sensor unit 202 allows wireless health monitoring signals acquisition via a sensors module 222. In a preferred embodiment, the sensor unit 202 is attached to the patient 220 via any suitable attachment means, such as a belt, an adhesive or any combination thereof. The sensor unit 202 may be an ultrasound sensor unit for use in ultrasound examinations.

For example, the sensor module may in various embodiments be a transducer array. The transducer array may include a plurality of transducer elements preferably arranged in a circular fashion with an at least one transducer element preferably positioned at the center of the array. The transducer elements may also be, in some aspects, piezoelectric transducers. The transducer array for the sensor module may receive various Doppler signals via a communications module or other control and communication electronics through, variously through wired cables or wireless connections.

Sensor unit 202 may further include capacitive or resistive sensors including touchscreens/touchpads which allow the operator to touch the surface of the sensor unit and which are detected by the sensor unit 202 through a plurality of reference sensor data. A plurality of sensors can be utilized to localize the position of the sensed touch by the operator on the surface of the device. The associated reference sensor data 304 are represented in the table of FIG. 3 and allow identification of a programmed or previously defined gesture. The corresponding sensors which read the gesture input can be a number of sensors or other sensor input apparatus in order for the sensor unit to detect a gesture. Gesture sensor data may then be transmitted to the base unit for corresponding determination of the represented gesture in the gesture database as well as the associated system functions. Alternatively, and in some implementations, the sensor unit may have a copy of the gesture database locally and could interpret sensor data and/or alternatively activate the corresponding system functions associated with the corresponding detected gesture template.

In some implementations, it may be desirable to prevent unwanted touches or actions from initiating system functions. Such undesirable interference actions may arise from the patient or the operator. In such instance and to avoid such initiation of undesired functionality, ready means to enable and disable gesture input should be implemented within the sensor unit. Proximity sensors detecting a gripping action of the sensor unit 202 may be used as well as other locking gestures or system inputs or settings.

In other implementations, a fingerprint sensor may be integrated with the sensor unit 202 wherein the sensor would allow for only authorized users to access various functional inputs. Finger print data may be maintained in the memory for persons having rights to manipulate transducer functionality and could be stored locally or in a similar database at the base unit. In such implementations, multiple users could have their fingerprints recorded for activation of the sensor unit or specific functionality. Finger print sensor data may be utilized to provide and define distinct profiles for each operator, set up routines or gesture inputs. As well, in embodiments, actions and/or functions could be associated with particular fingers applied to a fingerprint sensor. For example, an index finger input may provide specific predefined functionality while a middle finger could provide volume increase and ring finger could decrease the volume. Alternative associative functions could readily by defined for each finger of the authorized user.

In some instances, the sensors module 222 comprises an at least one ultrasound Doppler sensor for monitoring or measuring the fetal heart rate. The sensors assembly 222 also comprises a TOCO sensor for registering the uterine contractions. The sensor unit 202 is configured to dock on the docking port 212 of the base unit 200 when the wireless health monitoring system is not deployed or the sensor unit 202 is charging on the docking port 212. In an embodiment of the invention, more than one docking port 212 is provided on the base unit 200 for docking a plurality of sensor units. The sensor unit 202 comprises a power source 224, a communication module 226, an at least one accelerometer 228, and alternatively an audio output device 230. In one implementation of a system implementing the various features and aspects herein, communication modules 214 and 226 are communicatively coupled wirelessly but in some implementations through wired connectivity or if the sensor is docked for charging.

FIG. 3 illustrates a gesture template database according to another embodiment described herein. The gesture template database stores the gesture templates, each of which is assigned a gesture ID 300 and a gesture label 302. Also stored in the gesture template database are the corresponding sensor data 304 that allows identification of each gesture. The gesture template database also stores the system functions 306 assigned to each of the stored gesture templates. In various embodiments, the gesture template database 218 is stored in the memory of the base unit of the wireless health monitoring system. Alternatively, the gesture template database is stored in a local or remote network server. When the at least one sensor detects a performed gesture, the gesture template database is accessed by the system to identify the matching stored gesture template and the corresponding system function. The template database could be, depending on implementations, located at the sensor unit or at the base unit or, in the alternative, both wherein a master is maintained and kept at one or an alternative location. Further, in optional implementations, a master table may be located on the base unit and when the sensor unit is docked, transferred to the senor unit memory.

In some implementations, the gesture template database may be remote from the base unit 200 and may be available to include a standard library of gestures and associated definitions and system functions. These associated gestures of the gesture database may be reachable by the communication module and may include an online database.

As well, both the base unit and the sensor unit may include a separate processor with associated memory to allow for execution of programs implementing the various features and functions of the ultrasound sensor unit and the base unit. In some aspects, both the sensor unit and the base unit may be integrated in the same module and/or may execute programs from the same memory. Further, in various implementations, the gesture database may be accessible by one or both the base unit 200 and the sensor unit 202. Additionally, the display and or user interface 204/206 may be integrated with the base unit and or other aspects and structures of the system described herein may include shared memory and database access. The user interface may further include a display subsystem. The display subsystem may include a cathode ray tube (CRT), a flat-panel device such as a liquid crystal display (LCD), a projection device, or some other mechanism for creating a visible image. The display subsystem may also provide non-visual display such as via audio output devices. In general, use of the term output device and display/user interface is intended to include all possible types of devices and ways to output information from computing device to the user or to another machine or computing device.

Further, in some aspects, a storage subsystem may be used with the memory to store programming and data constructs that provide the functionality of some or all of the modules described herein including the gestures database. For example, a storage subsystem or other memory may include the logic to perform one or more aspects of the various methods described.

The software modules which implement the various features set out in the implementations are generally executed by a processor alone or in combination with other processors. Memory used in the various storage subsystems can include a number of memories including a main random access memory (RAM) for storage of instructions and data during program execution and a read only memory (ROM) in which fixed instructions are stored. A file storage subsystem may be used to provide persistent storage for program and data files, and may include a hard disk drive, a floppy disk drive along with associated removable media, a CD-ROM drive, an optical drive, or removable media cartridges. The modules implementing the functionality of certain implementations may be stored by the file storage subsystem in the storage subsystem, or in other machines accessible by the processor(s) described herein.

Further, a bus subsystem may provide a mechanism for letting the various components and subsystems of any computing device/base unit communicate with each other as intended. Although the bus subsystem may be a single bus, alternative implementations of the bus subsystem may use multiple busses to connect the various structures.

The computing device and/or base unit can be of varying types including a workstation, server, computing cluster, blade server, server farm, or any other data processing system or computing device which may be in communication with the ultrasound device. Due to the ever-changing nature of computers and networks, the description of the computing device and/or base unit and other system elements depicted in the various implementations is intended only as a specific example for purposes of illustrating some implementations. Many other configurations of a computing device are possible having more or fewer components than the computing device depicted in the figures.

In various implementations, access and modification of data stored in the gesture template database is restricted to authorized users, such as doctors and medical technicians, to prevent intentional or accidental tampering with the control gestures of the wireless health monitoring system. This can be implemented using standard security systems and methods such as requiring a password or other security identification inputs to access a gestures customization interface, for example, that is only accessible to authorized users. Other security features may be implemented in the present invention.

In some implementations of the technology described herein, gesture templates corresponding to commonly-used gestures are pre-stored in the gesture template database with assigned default system functions. Examples of these commonly-used gestures are simple finger gestures, such as single tap, double-tap, or directional swiping. More complex gesture templates that combine various sliding, swiping, pinching and rotational motions may be stored for activating more complex functions. Other types of gesture templates that can be used according to the present invention include combinations of gestures separated by sort time intervals such as those that require tapping multiple times in quick succession to enable a customized function, either as a series of the same tapping motions or in combination with other types of gestures.

In another aspect, a combination of two or more functions is assigned to one gesture template, so a user can enable at least two successive functions using only one gesture. Optionally, the default system functions of the pre-stored gestures can be modified by the user so that the gestures activate other non-standard or non-default functions.

Figure 4:
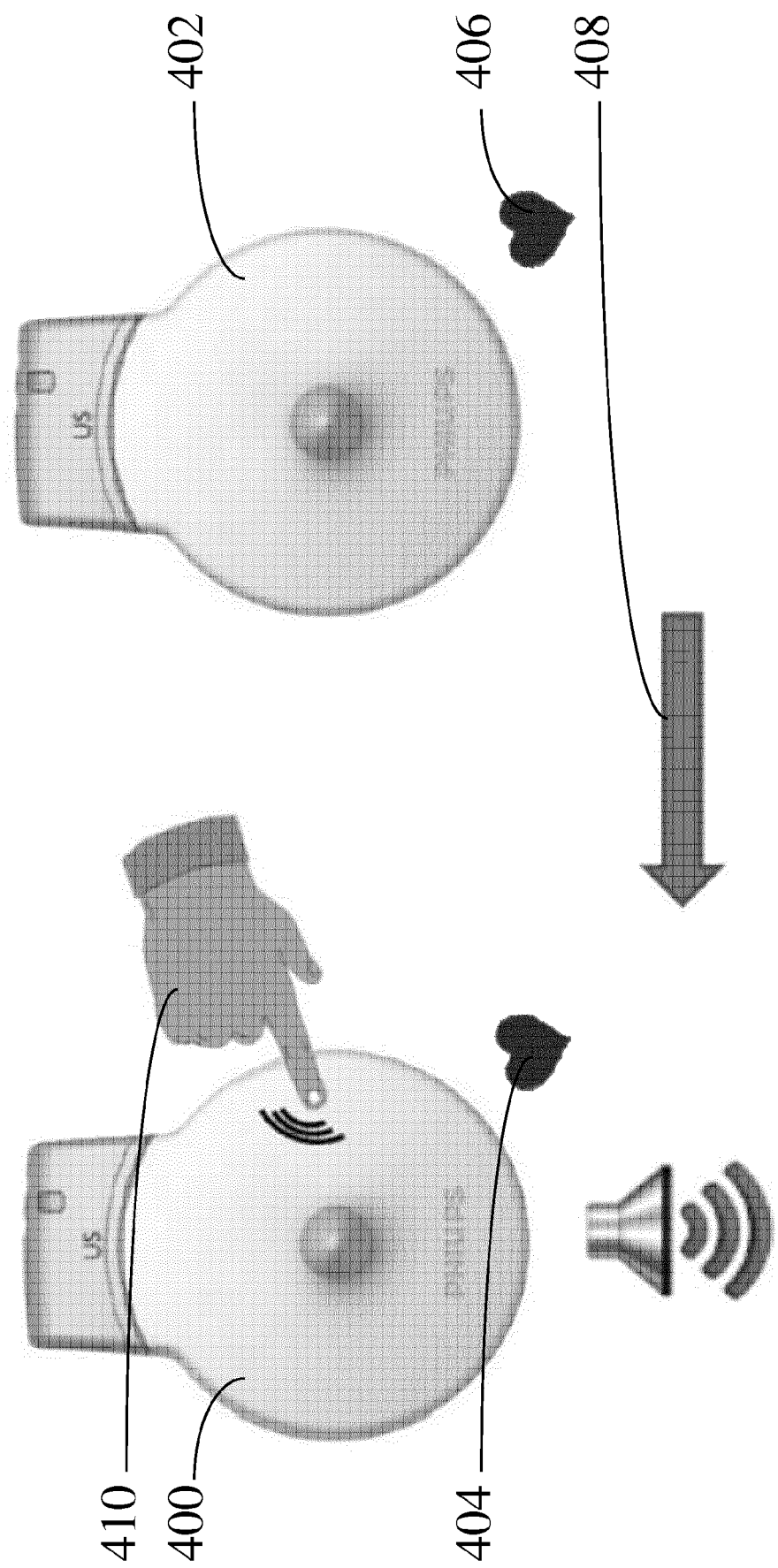
FIG. 4 illustrates a wireless health monitoring system using a sensor for sound source switching via a gesture between two wireless sensors for the fetal monitoring of twins.

FIG. 4 illustrates a wireless health monitoring system using a system function for sound source switching between two sensors for the fetal monitoring of twins. In this case, two sensors 400, 402 are attached to the abdomen of a patient expecting twins in order to monitor the two fetal hearts 404, 406, respectively. Only one of the two sensors 400, 402 can be used as the source of the acoustical output to monitor one particular fetal heart. For example, a doctor may use the wireless health monitoring system for monitoring of a patient's twins during labor. The doctor attaches the two sensors 400 and 402 on the patient's abdomen for monitoring fetal hearts 404 and 406, respectively. The doctor monitors the fetal heart 406 first and uses sensor 402 as the sound source of the system. To monitor fetal heart 404 next, a sound-source-switch (signified by arrow 408) from sensor 402 to sensor 400 must be activated. To activate the sound-source-switch 408, the doctor performs a corresponding control gesture 410 (illustrated here as a tap) on sensor 400. After detecting the performed gesture 410 by the sensor 400, the sound-source-switch 408 is activated and sensor 400 becomes the sound source of the system. This control gesture-activated sound-source-switch, which does away with the need to use physical buttons, enables the doctor to alternately monitor fetal hearts 404 and 406 quickly and conveniently because the doctor no longer needs to move back and forth between the base unit and the patient.

Figure 5:
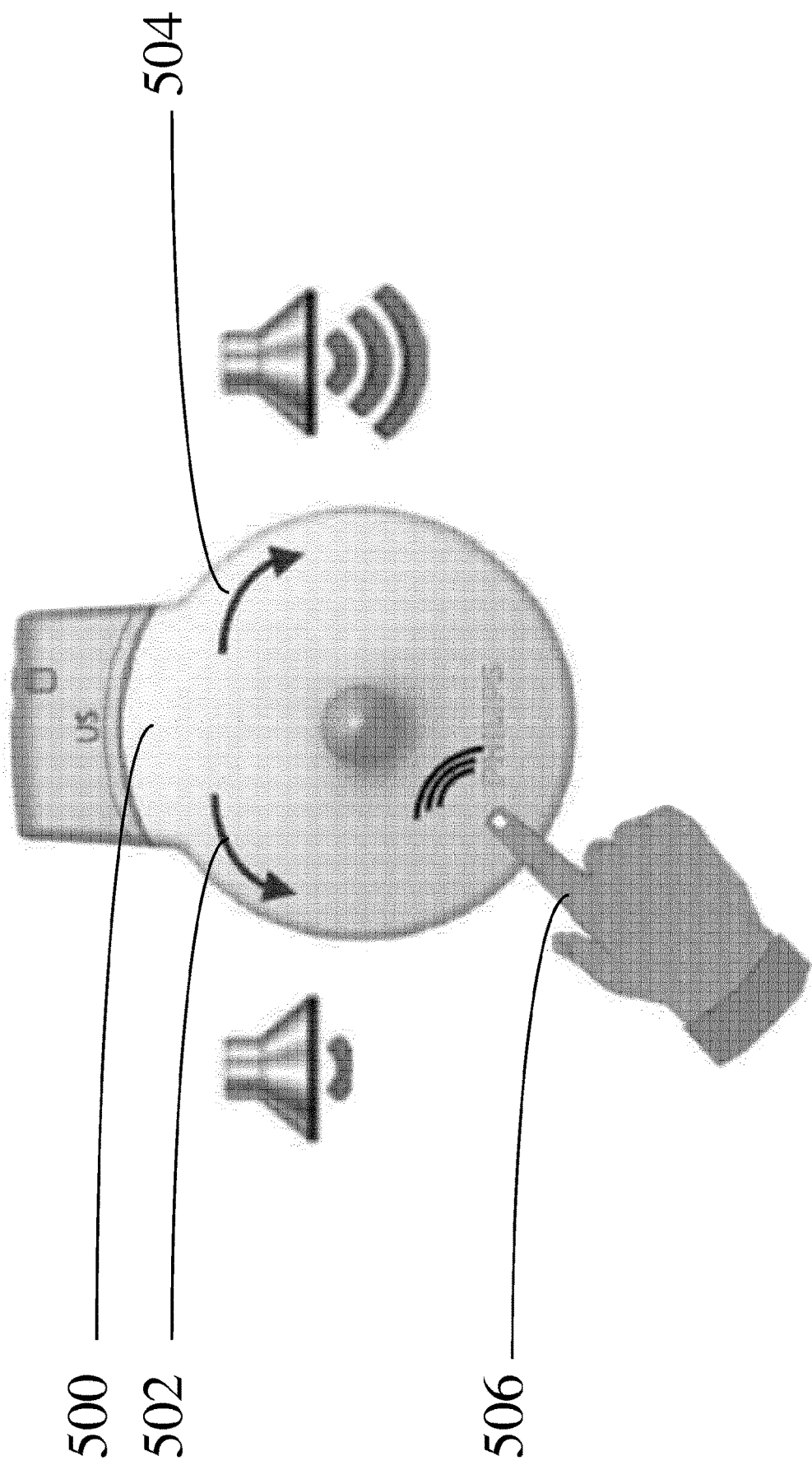
FIG. 5 illustrates a wireless health monitoring system using a sensor for volume adjustment via a gesture.

FIG. 5 illustrates a wireless health monitoring system using a system function for volume adjustment of the system's audio output. In using the wireless health monitoring system, the sensor 500 detects a fetal heart and outputs the detected fetal heartbeat. As illustrated in FIG. 5, a counterclockwise swiping motion 502 or a clockwise swiping motion 504 detected by a sensor 500 are used by the user 506 to adjust the volume when the system is in the volume adjustment mode. The control gestures 502 and 504 correspond to decreasing and increasing the sound volume, respectively, analogous to the rotation of a volume control knob. After adjusting the volume to a desired level via the control gestures, the volume adjustment mode is preferably deactivated by a timeout or another control gesture.

The audio output device, as noted, can be located on the sensor unit 202 or integrated within the base unit 200. The audio output device, whether located at the base unit or the sensor unit, could receive as input the signals from the sensor module and convert such signals to audio stream signals which are emitted by the output device. Conversion of such signals to audio format could be accomplished either at the base unit or the sensor unit. In implementations, the audio output device 230 is located on the base unit which is in direct communication with the sensor unit and which receives via a communication channel and the communication modules 214/224 the reflected ultrasonic signal stream from the sensor unit for creation of an audio stream.

Figure 6:
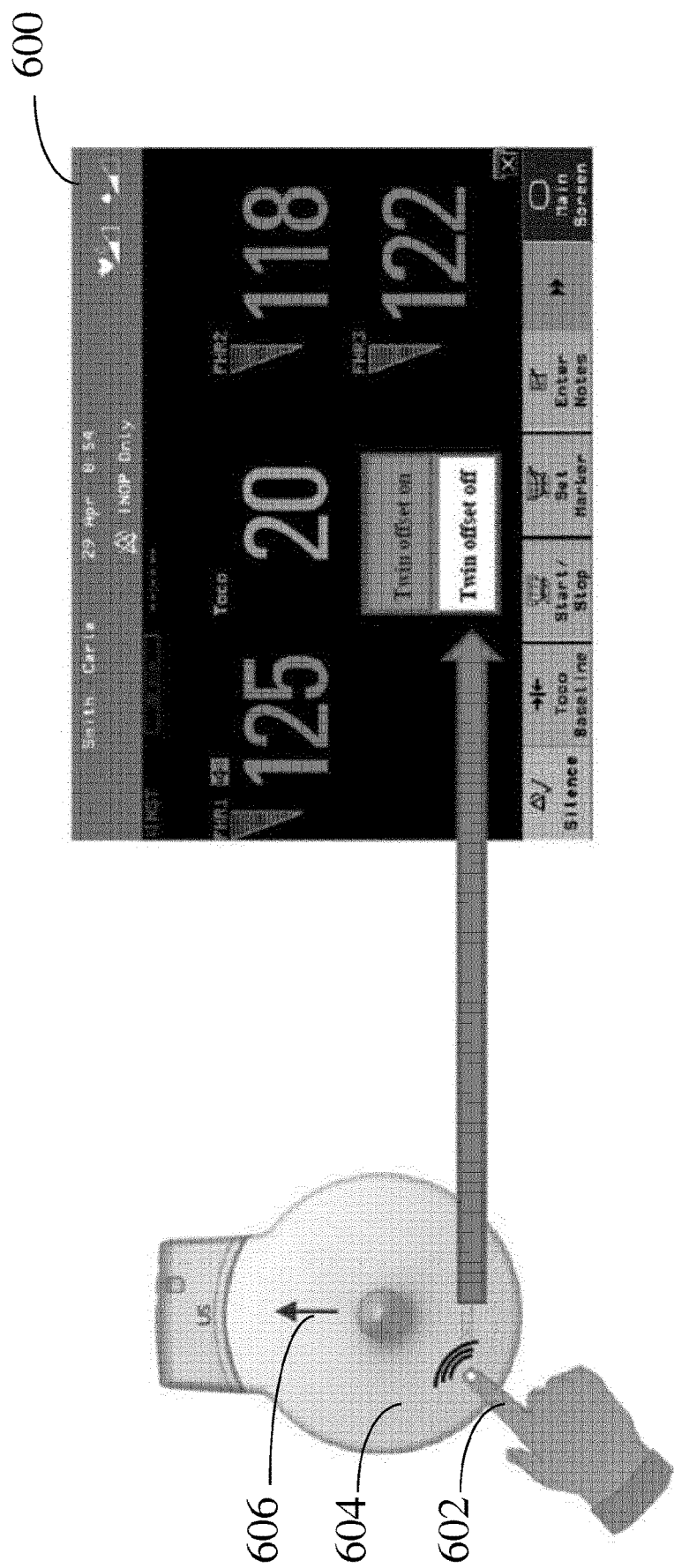
FIG. 6 illustrates a wireless health monitoring system using a sensor for inputting mouse-type function via a gesture on a wireless health monitoring system GUI.

FIG. 6 illustrates a wireless health monitoring system according to another embodiment described herein which recognizes mouse-type inputs on a wireless health monitoring system GUI 600 on the system's display. Similar to the volume adjustment mode, a mouse-type input mode is activated via a specific control gesture performed by a user 602 on the sensor 604. Once the mouse-type input mode is activated, the sensor detects and interprets control gestures that correspond to mouse-type inputs (e.g., clicking, cursor navigation) on the GUI 600. Here, swiping up on the sensor 604 corresponds to an upward movement of the cursor on the GUI 600, swiping down corresponds to a downward movement of the cursor, and similarly for swiping left and right. Other gestures in this mode, such as tapping, may also be used to activate a click or select function on the GUI 600. In FIG. 6, the "Twin offset on" button is selected by performing an upward swiping 606 and the corresponding function activated via a tap or a double-tap. When the user is done, the mouse-type input mode is deactivated by another control gesture.

In another implementation of the technology disclosed herein, a doctor or other operator may decide to customize the control gesture for activating a standby mode of the wireless health monitoring system. As shown, a gesture-lock mode deactivates the gesture detection of the sensor, which is useful when handling the sensor during monitoring and no adjustments are needed to be made. The operator may enter a control gesture customization mode on the wireless health monitoring system, which requires him to input a password before he is allowed to create a new gesture template. The new gesture for example, a pattern of four quick consecutive taps may be performed by the operator and detected via the accelerometer connected to the sensor. Preferably, the operator is prompted to repeat the new gesture a certain number of times to calibrate the accelerometer and allow accurate detection of the gesture before storing it as a gesture template. Once stored as a gesture template in the gesture template database, the doctor selects and assigns the gesture-lock functionality to the new gesture template. The operator confirms the selection and saves the changes made to the gesture template database. After saving the changes in the gesture template database, the wireless health monitoring system now associates the stored gesture template with the selected gesture-lock function. Thus, when the operator performs the four quick consecutive taps on the sensor unit during a monitoring session, the sensor detects the said gesture and the system then performs the previously assigned function, which is a gesture-lock.

In another aspect, the system functions include a system configuration of the wireless health monitoring system. For example, a medical technician was instructed to create a health monitoring system configuration designed for obese patients. It is known that thick abdominal fat layers interfere with the effectiveness of ultrasound health monitoring. A system configuration for obese patients may specify a higher intensity setting and/or specific frequency adjustments of the ultrasound waves to be emitted by the sensor unit. The medical technician saves this specific system configuration as a system function, which is assignable to a specific gesture template, such as tracing a triangle pattern on the sensor unit.

Thus, when a monitoring session calls for the use of the previously stored configuration, an authorized medical personnel need only perform the triangle pattern gesture on the wireless sensor in order to activate the obese patient system configuration. This prevents unnecessary repetition of manual, step-by-step system configuration of the same settings every time a session involves an obese patient. This procedure also improves consistency, reliability, and predictability of results from the monitoring sessions, aside from making the operation of the system much more convenient and simpler to perform. Other system configurations appropriate to different situations may be similarly implemented via gesture-function customizations.

In yet another embodiment of the invention, the system functions include a personnel alert. By assigning a gesture that corresponds to sending an alert to the base unit or medical personnel, the patient is provided an immediate means to communicate an emergency during labor monitoring. Providing a personnel alert function on the wireless sensor further allows the patient's freedom of motion, since the patient does not need to restrict herself in an area within easy access of a fixed emergency call button, usually disposed near a patient's hospital bed. For example, a patient admitted in early hours of labor is monitored using the wireless health monitoring system. Should the patient need immediate medical attention, she can readily perform the corresponding alert gesture on the wireless sensor attached to her abdomen and activate a personnel alert. After receiving the alert, medical personnel can then immediately respond to the patient.

The present invention is not intended to be restricted to the several exemplary embodiments of the invention described above. Other variations that may be envisioned by those skilled in the art are intended to fall within the disclosure.

The invention claimed is:

1. A method for controlling an ultrasound system comprising at least two ultrasound sensor units using gestures, each ultrasound sensor unit comprising a sensor for gesture detection on a surface of the ultrasound sensor unit and the method comprising:
   detecting a gesture on a first ultrasound sensor unit;
   determining if the detected gesture matches a gesture stored in a gesture database;
   matching the detected gesture to the gesture in the gesture database;
   reading an assigned at least one system function in the gesture database related to the detected gesture; and
   activating the at least one system function,
   wherein the at least one system function includes switching a sound source from a second ultrasound sensor unit to said first ultrasound sensor unit and wherein the gesture assigned to this system function comprises a double-tap on said surface of the first ultrasound sensor unit.

2. The method of claim 1 wherein the sensor for detecting gestures comprises at least one capacitive sensor.

3. The method of claim 1 further comprising:
   populating the gesture database by storing a further gesture detected on the surface of the first or second ultrasound unit as a gesture template in the gesture data base;
   assigning at least one system function to the stored gesture in the gesture data base;
   including with the detected gesture a plurality of reference sensor data.

4. The method of claim 1 further comprising:
   activating mouse-type input mode at the first or second ultrasound sensor unit by recognizing an associated mouse-type input mode gesture by means of the sensor of the respective ultrasound sensor unit;
   interpreting control gestures on the respective ultrasound sensor unit for an associated graphical user interface display.

5. The method of claim 4 wherein the interpreting control gestures relates to input on the graphical user interface display.

6. The method of claim 1, wherein the at least one system function comprises an adjustment of a volume and wherein the gesture assigned to this system function comprising a counterclockwise swiping motion or a clockwise swiping motion.

7. The method of claim 1 further comprising providing the detected gesture to a base unit, wherein the determining if the detected gesture matches the gesture stored in the gesture database is performed by the base unit.

8. The method of claim 1 wherein the determining if the detected gesture matches the gesture stored in the gesture database is performed by the first ultrasound sensor unit.

9. The method of claim 1, wherein each of the ultrasound sensor units comprises an accelerometer for monitoring or measurement of one or more physiological parameters, and wherein the sensor for gesture detection is provided by said accelerometer.

10. The method of claim 1, wherein the ultrasound sensor units are each adapted for attaching to a patient's body.

11. An ultrasound system comprising at least two ultrasound sensor units controllable using gestures, each ultrasound sensor unit comprising a sensor for gesture detection on a surface of the ultrasound sensor unit, wherein the system is configured
   to determine if a gesture detected on a first ultrasound sensor unit matches a gestures stored in a gesture database,
   to match the detected gesture to the gesture in the gesture database,
   to read an assigned at least one system function in the gesture database related to the detected gesture, and
   to activate the at least one system function, and
   wherein at least one system function includes switching a sound source from a second ultrasound sensor to said first ultrasound sensor unit and wherein the gesture assigned to this system function comprises a double-tap on the surface of the first ultrasound sensor unit.

12. The system of claim 11, further comprising a base unit including a processor and memory and further comprising a control gesture data database accessible by the processor of the base unit;
   wherein the ultrasound sensor units are operable to:
   detect gesture sensor data representing a gesture;
   provide the detected gesture sensor data to the base unit by electronic communication;
   wherein the memory on the base unit includes instructions which, when executed by the processor, operate to:
   determine if the detected gesture sensor data matches one of a plurality of gestures stored in the gestures database;
   read the assigned at least one system function in the gesture database related to the determined matched gesture;
   activate the at least one system function.

13. The system of claim 12 wherein the memory on the base unit further includes instructions which, when executed by the processor, operate to:
   populate the gesture database by storing detected gesture sensor data as a gesture template in the gesture database;
   assign an at least one system function to the stored gesture in the gesture database.

14. The system of claim 12 wherein the detected gesture sensor data represents a fingerprint, and optionally wherein the gesture database includes entries representative of a plurality of operator fingerprints and wherein the associated system function is an operator profile.

15. The system of claim 12 wherein the base unit is further operable to activate mouse-type input mode at the first or second ultrasound sensor unit by recognizing an associated mouse-type input mode gesture;

interpret control gestures on the respective ultrasound sensor unit for an associated graphical user interface display, wherein the control gestures relate to input on a graphical user interface display.

* * * * *